US 11,331,553 B2

United States Patent
D'Alesio

(10) Patent No.: US 11,331,553 B2
(45) Date of Patent: May 17, 2022

(54) SYSTEM FOR PERFORMING MOTOR ACTIVITY

(71) Applicant: REAXING S.R.L., Milan (IT)

(72) Inventor: Gionata D'Alesio, Milan (IT)

(73) Assignee: REAXING S.R.L., Milan (IT)

( * ) Notice: Subject to any disclaimer, the term of this patent is extended or adjusted under 35 U.S.C. 154(b) by 669 days.

(21) Appl. No.: 16/091,763

(22) PCT Filed: Apr. 6, 2017

(86) PCT No.: PCT/IB2017/051989
§ 371 (c)(1),
(2) Date: Oct. 5, 2018

(87) PCT Pub. No.: WO2017/175175
PCT Pub. Date: Oct. 12, 2017

(65) Prior Publication Data
US 2019/0091537 A1    Mar. 28, 2019

(30) Foreign Application Priority Data
Apr. 6, 2016 (IT) .......................... UA2016A002341

(51) Int. Cl.
*A61B 5/00* (2006.01)
*A63B 69/00* (2006.01)
(Continued)

(52) U.S. Cl.
CPC .......... *A63B 69/0053* (2013.01); *A61B 5/024* (2013.01); *A61B 5/1112* (2013.01);
(Continued)

(58) Field of Classification Search
CPC combination set(s) only.
See application file for complete search history.

(56) References Cited

U.S. PATENT DOCUMENTS 5,938,564 A * 8/1999 Bachman ................. A63K 1/02
                                                        482/3
6,428,449 B1 * 8/2002 Apseloff ............ A63B 71/0622
                                                        482/3
(Continued)

FOREIGN PATENT DOCUMENTS

EP    2 564 901    3/2013
GB    2 500 058    9/2013
(Continued)

OTHER PUBLICATIONS

International Search Report, PCT/IB2017/051989, dated Sep. 14, 2017.
Written Opinion, PCT/IB2017/051989, dated Sep. 14, 2017.

*Primary Examiner* — Shirley X Jian
(74) *Attorney, Agent, or Firm* — Nixon & Vanderhye

(57) ABSTRACT

Disclosed is a system for performing motor activity, including a plurality of modular devices, each modular device including a unit for generating at least one sensory stimulus, a generation unit activation unit and a mechanism for detecting a human reaction to the stimuli, there being provided an external control unit intended to generate commands for the activation unit of each modular device. The external control unit includes a unit for measuring the parameters acquired by one or more sensors associated with the body of at least one person.

10 Claims, 1 Drawing Sheet

(51) Int. Cl.
*A63B 71/06* (2006.01)
*A63B 24/00* (2006.01)
*A61B 5/024* (2006.01)
*A61B 5/11* (2006.01)
*G06F 3/01* (2006.01)
*G06F 3/16* (2006.01)
*G09B 19/00* (2006.01)

(52) U.S. Cl.
CPC ............ *A61B 5/1123* (2013.01); *A61B 5/486* (2013.01); *A61B 5/749* (2013.01); *A63B 24/0062* (2013.01); *A63B 24/0087* (2013.01); *A63B 71/0622* (2013.01); *G06F 3/017* (2013.01); *G06F 3/167* (2013.01); *G09B 19/0038* (2013.01); *A61B 2503/10* (2013.01); *A61B 2560/0443* (2013.01); *A61B 2562/0204* (2013.01); *A61B 2562/0257* (2013.01); *A63B 2071/068* (2013.01); *A63B 2071/0625* (2013.01); *A63B 2071/0677* (2013.01); *A63B 2071/0683* (2013.01); *A63B 2071/0694* (2013.01); *A63B 2209/08* (2013.01); *A63B 2220/12* (2013.01); *A63B 2220/803* (2013.01); *A63B 2220/805* (2013.01); *A63B 2220/808* (2013.01); *A63B 2220/833* (2013.01); *A63B 2220/836* (2013.01); *A63B 2225/10* (2013.01); *A63B 2225/20* (2013.01); *A63B 2225/50* (2013.01); *A63B 2225/74* (2020.08); *A63B 2230/062* (2013.01)

(56) References Cited

U.S. PATENT DOCUMENTS

| | | | |
|---|---|---|---|
| 7,625,314 B2 * | 12/2009 | Ungari | A63B 69/0053 482/1 |
| 7,658,694 B2 * | 2/2010 | Ungari | A63B 69/345 482/1 |
| 7,720,572 B2 * | 5/2010 | Ziegler | B25J 5/007 713/153 |
| 7,963,885 B2 * | 6/2011 | Mazzanobile | A63B 69/0028 482/4 |
| 8,702,538 B1 * | 4/2014 | Coffin | G09B 9/006 473/422 |
| 8,702,566 B2 * | 4/2014 | Mazzanobile | A63B 26/003 482/4 |
| 9,055,791 B2 | 6/2015 | Proud et al. | |
| 10,722,775 B2 * | 7/2020 | Black | A63B 69/0028 |
| 2008/0269016 A1 * | 10/2008 | Ungari | A63B 69/0053 482/1 |
| 2014/0070957 A1 | 3/2014 | Longinotti-Buitoni et al. | |
| 2014/0257741 A1 * | 9/2014 | Chupp | G01G 23/3728 702/173 |
| 2014/0361875 A1 * | 12/2014 | O'Hagan | G09B 19/0038 340/8.1 |
| 2015/0040282 A1 | 2/2015 | Longinotti-Buitoni et al. | |
| 2015/0174441 A1 | 6/2015 | Junaid et al. | |
| 2015/0366504 A1 | 12/2015 | Connor | |

FOREIGN PATENT DOCUMENTS

| | | |
|---|---|---|
| WO | WO 2007/142588 | 12/2007 |
| WO | WO 2010/044666 | 4/2010 |
| WO | WO 2014/151880 | 9/2014 |
| WO | WO 2015/061676 | 4/2015 |

* cited by examiner

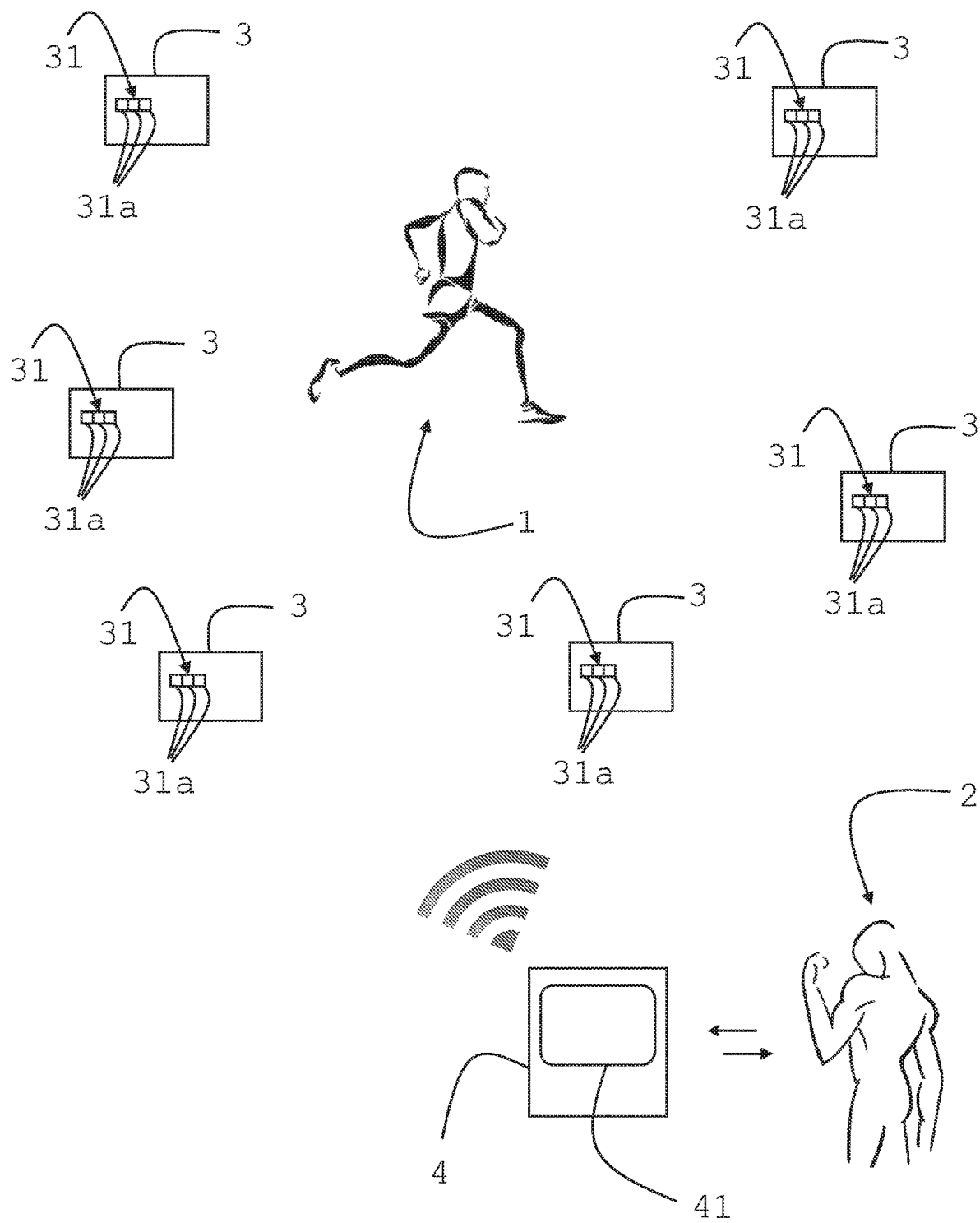

SYSTEM FOR PERFORMING MOTOR ACTIVITY

BACKGROUND OF THE INVENTION

Field of the Invention

The present invention relates to a system for performing motor activity.

The system comprises a plurality of modular devices, each modular device comprising means of generating at least one sensory stimulus, a generation means activation unit and means of detecting a human reaction to said stimuli.

It is also provided with an external control unit intended to generate commands for the activation unit of each modular device.

The present invention relates in general to sports development and training systems and, in particular, refers to speed, resistance, force and coordination training, development and rehabilitation of the body of a person.

Description of the Related Art

Various systems produced as described above are known in the field, consisting of modular devices that are arranged on a training ground randomly or according to predefined patterns.

The alternating activation of each modular device generates stimuli adapted to stimulate a reaction of a person who has to train, who must move between one modular device and the other based on their activation and interact with these modular devices.

These known training systems generally comprise modular electronic devices equipped with light sources that are activated alternately according to a specific sequence. The modular devices are also provided with sensors adapted to detect the presence of an object nearby and are configured to deactivate said light source when an object is detected within a specific range of action of the sensor. The person performing an exercise must bring a part of the body close to an illuminated device to deactivate the light source. These systems are generally configured to activate the light source of one or more modular devices when the respective source of a device has been deactivated by the movement of the person. The sequence of activations obliges the person to move on the training ground between the various modular devices more or less rapidly, as a function of the activation and deactivation speed of the light sources.

The frequency of activation and the positioning of the modular devices (size of the training ground) thus allow a wide range of training operations, for one or more people, even with very different motor capacities and physical prowess.

From the above it is evident how a fundamental aspect of the prior art systems is programming of the activation of the modular devices, or rather of the light sources, so as to ensure effective training sessions at all times.

Generally, known systems have a control unit that supervises activation of the modular devices and that has stored programs that autonomously activate the devices according to a specific sequence and at predetermined times, generating training programs.

However, with the use of preset programs, it is not possible to obtain a high level of adaptability of the training session as a function of the person to be trained, for example a professional athlete or a person who requires rehabilitation. The use of these programs also requires the modular devices to be arranged in precise positions in the training area.

To overcome these limits, some known systems comprise a control interface, for example usable by a trainer, with which this latter can supervise activation of the modular devices, generating a specific sequence of activations.

The trainer can thus adapt the training session based on the person's needs and as a function of the capacities and of the physical condition of this latter.

The control interface of known systems generally consists of a portable device, such as a tablet or the like, that communicates in wireless mode with the modular devices.

However, this improvement is not particularly useful in the case of a training session during which the athlete must make sudden or unexpected movements or involving complex or structured activation sequences. In fact, the trainer could encounter difficulties in interacting with this control interface in order to manage activation of the modular devices.

Therefore, there is the need to provide a training system that overcomes the limits of the known systems described above.

BRIEF SUMMARY OF THE INVENTION

In this context, the object of the invention is to propose a training system in which the sequence of activations of the modular devices can be controlled in a more practical and intuitive manner.

In particular, the object of the invention is to propose a training system in which a person in charge of controlling the system, for example a trainer, can manage activation of the modular devices in real time without using the control interface.

The object of the invention is also to provide a dynamic training system in which the modular devices are moved on the training ground.

A further object of the invention is to produce a training system that provides the person training with advance stimulation to teach the person to carry out specific complex movements.

The present invention achieves the objects set through a system for performing motor activity comprising a plurality of modular devices, where each modular device comprises at least:
 means of generating at least one sensory stimulus;
 a generation means activation unit; and
 means of detecting a human reaction to said sensory stimuli.

According to the invention, the system also comprises a control unit intended to generate commands for the activation unit of each modular device. Said control unit, in turn, comprises means for measuring the parameters acquired by at least:
 one or more sensors associated with the body of at least one person, for example a trainer or the person training; and
 one or more position sensors mounted on the modular device or on a supporting structure of said modular devices.

Moreover, said control unit is configured to generate said commands for the activation unit of the modular devices as a function of the parameters acquired by the aforesaid sensors.

As will be more apparent from the following description, if the one or more sensors are associated with the body of a trainer, or a person in charge of controlling the system, optionally also the user, it is possible for gestures of the body of the trainer or voice commands to be detected by detection means and generate signals for activation of the modular devices.

To this end, according to an aspect of the invention, said sensor to be associated with the body of a person can comprise at least one microphone associated with a voice-recognition system. The system can optionally also, or alternatively, comprise a sensor configured to detect movements or gestures of the body. Based on movements of the limbs, or of other parts of the body, different modular devices can be activated or, for example, the type of stimulation to be activated (color of the lights, etc.) can be selected. Sensors suitable for this purpose are, for example, accelerometers.

This configuration allows rapid activation of the modular devices to be achieved, as this activation is generated by movements or by actions of the body of the trainer, which are executed in more sudden manner than a command imparted with an external control interface of known type.

The aforesaid system thus has an activation speed of the modular devices typical of an automatic system, with the versatility and adaptability of a training program managed by a trainer.

According to another aspect of the invention, the system can be configured to generate said activation commands of the modular devices as a function of the movements of the body of the person performing the exercise. According to this variant, said sensor to be associated with the body of the person can comprise at least one accelerometer, or equivalent sensors, or a geolocation sensor.

Also in this case, the control unit can generate specific commands, for example decide which modular device to activate or in which instant, as a function of the gesture that the person is carrying out, or of his/her position in the training area.

According to another aspect of the invention, said sensor to associate with the body of the person can be a sensor of biometric type, generally attached to the person training, adapted to detect a biometric parameter of this latter. Said sensor can, for example, comprise a heart rate monitor. According to this variant, alternative to or combinable with those described above, the control unit can generate said activation commands as a function of the physical conditions of the person training, for example reducing the frequency of the activations in the case of excessive fatigue of the person, or vice versa.

In all the variants described above, the aforesaid sensors can be included in the training system according to the present invention. If the sensors are not included, the control unit is in any case programmed to interact with said sensors, i.e. to receive the parameters measured by the sensors and, as a function of these, to control the activation units of the modular devices.

According to a possible embodiment, the control unit, whether external or integrated in one of the modular devices, comprises processor means for running a logical program, the running of which is responsible for generating command signals for controlling the activation units.

Advantageously, the system of the present invention can thus be provided with preset training programs, managed by running the logical program. Nonetheless, these programs can be modified based, for example, on the instructions or on the commands imparted by the trainer and detected by the detection means following a movement of this latter or by a voice command.

It is clear how this aspect is particularly advantageous: based on the features described, the system of the present invention can operate in a completely automatic manner, but this operation can be modified based on the decisions of the trainer or based on parameters relating to the person performing the training.

In order to ensure this dual function, the system of the present invention can advantageously comprise at least one display unit and an input-output interface.

Naturally, the display unit and the input-output interface can be integrated inside the control unit, if it is external, which can be in the form of portable device, such as a tablet, smartphone or the like, as described above.

According to a preferred embodiment, the means of generating at least one sensory stimulus comprise at least one source for the generation of light energy.

According to this configuration, the modular devices alternately emit a light, of various colors. During training the athlete must move toward the modular device emitting this light and switch it off.

Switching off can be performed in any known way, but advantageously takes place automatically when the athlete moves within a specific distance of the modular device.

For this reason, the means of detecting a human reaction preferably comprise a proximity sensor.

As soon as the detection means detect the presence of the athlete, they deactivate the generation of light by a modular device, to activate another and so forth for the entire duration of the training session.

In a possible variant, the source for the generation of light energy can comprise a display capable of projecting colors, images or messages. Typically, said source is an LCD panel or the like. According to this variant, the control unit sends the activation unit of the modular devices information in the form of images or messages projected on said display.

The user can therefore, in addition to identifying the modular device to move towards in order to deactivate it, also receive any instructions for carrying out specific more or less complex movements.

According to another embodiment of the invention, each modular device comprises a position sensor and preferably a geolocation unit.

The presence of the geolocation unit facilitates positioning of each single modular device.

In fact, the modular devices can be positioned on the training ground according to predefined patterns, which can be easily reproduced through correct identification of the position of each modular device.

Advantageously, in order to increase the portability of the parts of the system, each modular device has a rechargeable battery.

A container for housing the modular devices, comprising circuits for recharging the batteries of the modular devices, is also provided.

According to this configuration, once placed inside the container at the end of the training session, the modular devices can be easily charged, even during transport.

According to another variant of the invention, the training system can comprise a supporting structure on which the modular devices are fitted. According to an aspect of the invention, said structure can comprise one or more movable supports to which one or more modular devices can be fastened. The structure is preferably equipped with one or more sensors adapted to detect the position or the movements of one or more modular devices.

In this variant, the control unit is configured to receive the parameters detected by said sensors and control the activation units of the modular devices accordingly.

In particular, the control unit can determine the activation of a specific modular device when this, or another, is in a specific position of the structure.

Suitable position sensors are, for example, proximity sensors, accelerometers, geolocation units or the like.

BRIEF DESCRIPTION OF THE DRAWING FIGURE

These and other features and advantages of the present invention will be more apparent from the description below of some examples of embodiment, with reference to the attached FIG. 1, which illustrates a functional diagram of a variant of the device of the present invention.

DETAILED DESCRIPTION OF THE PREFERRED EMBODIMENTS

It is specified that the FIGURE attached to this patent application show some embodiments of the system for performing motor activity of the present invention, to better understand the advantages and the features thereof.

Therefore, these embodiments must be intended purely for illustrative purposes and do not limit the inventive concept of the present invention, i.e. that of producing a system that allows training instructions to be received both automatically and manually, so as to perform an effective training session supervised by a person with expertise.

FIG. 1 illustrates a functional diagram of a variant of embodiment of the system for performing motor activities of the present invention.

In accordance with FIG. 1, the system is used by two people, an athlete 1 who is training and a trainer 2 who establishes the training method.

The system comprises a plurality of modular devices 3 arranged inside a training environment.

Each modular device 3 comprises means of generating at least one sensory stimulus 31, a generation means activation unit and means of detecting a human reaction to the stimuli.

The system also comprises an external control unit 4 intended to generate commands for the activation unit of each modular device 3.

In the particular case illustrated in FIG. 1, the means of generating at least one sensory stimulus 31 consist of a series of high efficiency 3 color (RGB) LEDs 31a, which are activated by a circuit board, which forms the activation unit.

Each modular device 3 also comprises a rechargeable battery, not illustrated, and is identified by a unique identification code.

The unique identification code can, for example, consist of a number identifying the modular device of reference.

In this case, the upper part of each modular device 3 can consist of a transparent satin-finish methacrylate panel indicating the identification number.

In this way both the athlete 1 and the trainer 2 can easily identify each modular device 3.

A description of an example of embodiment of a modular device 3 can be found in the document WO2007/142588, the description of which is to be deemed an integral part of the present patent application.

Each modular device 3 communicates, preferably in wireless mode, with the external control unit 4 and receives from this latter, according to specific programs or communications modes, the commands for switching on the LEDs 31.

The external control unit 4 can, for example, consist of a portable device 4 controlled by the trainer 2.

The athlete 1 must each time reach the modular device 3 that is switched on and switch it off.

The LEDs 31 can be switched off according to different methods, but preferably the LEDs 31 switch off automatically when the athlete 1 is at a specific distance from the modular device 3 that is switched on.

For this reason the means of detecting a human reaction, belonging to each modular device 3, comprise a proximity sensor.

The proximity sensor detects the presence of the body of the athlete 1 and controls switching off of the LEDs 31, so that the LEDs 31 of one or more of the other modular devices can be activated.

The proximity sensor can, for example, consist of a photocell or of another proximity detection device, preferably positioned in the upper part of the modular device 3.

Once switched off, the modular device 3 communicates its condition to the control unit 4, to thus allow subsequent or simultaneous switching on of another or of other modular devices 3 and so forth.

The 3 color (RGB) LEDs 31 can generate six different light colors also to allow training sessions in pairs or in groups.

Advantageously, the modular devices 3 have, at the base, a suitable system of permanent magnets that allow them to also be attached to vertical walls or ceilings.

According to an embodiment, the modular devices 3 have a supplementary socket for charging the batteries, to allow, if required, permanent housing of the modular devices 3 in a supporting structure.

Preferably, the modular devices also comprise a circuit breaker for switching on/off.

According to the system of the present invention, the external control unit 4 comprises means for measuring the parameters acquired by one or more sensors associated with the body of at least one user.

With particular reference to FIG. 1, the sensor can be associated with the body of the athlete 1 or of the trainer 2 and communicates information to the means for detecting the parameters of the external control unit 4, so as to generate command signals for operation of the activation units of the modular devices 3.

It is clear how these command signals are generated by the trainer 2 or by the athlete 1.

As already mentioned, these command signals can be provided in combination with operation of the automatic system, i.e. of an activation of the activation means managed by a logical program that has specific operating logics or training programs.

In fact, the external control unit 4 advantageously comprises processor means for running a logical program, the running of which is responsible for generating command signals for controlling the activation units.

The trainer 2 can supervise automatic operation of the system, generating command signals that will have priority over the operating modes.

According to a first embodiment, the sensor associated with the body of a user comprises at least one microphone connected to a voice-recognition system.

According to this configuration, the trainer 2 has a microphone that detects orders imparted by voice that are processed by the voice-recognition system.

The trainer 2 can, for example, indicate the number of the modular device 3 to be switched on and, optionally, the color of the LED 31 that must be switched on.

Alternatively or in combination, it is possible for the sensor associated with the body of a person, trainer or athlete, to include a system for detecting movements and/or gestures of the body.

In this case, the trainer 2 can have an accelerometer for one or more limbs and based on the movement can activate a different modular device 3.

It is clear how, in this case, activation of the activation means is faster; the trainer 2, simply by moving an arm or speaking, can activate a specific modular device 3.

The external control unit 4 can obviously be produced as a portable device, such as a tablet or the like, having a display unit and an input-output interface.

The display unit and the input-output interface can be integrated inside a single touch screen 41, as illustrated in FIG. 1.

The external control unit 4 communicates with each modular device 3 imparting the sequential switch on logics and will have the task of sending feedback on the training session of the athlete 1 according to specific methods. Direct communication between the external control unit 4 and the modular devices 3 ensures immediate response times without delays of any sort. The fact that the trainer 2 can supervise operation of the system according to the methods described above, will allow, above all during group training sessions, the selection of programs and switching on of the modular devices 3 in real time.

According to a possible embodiment, the athlete 1 can also supervise operation of the system. In this variant, the sensor associated with the body of a person, preferably the athlete, comprises sensors for detecting the biometric parameters of the body of the person.

For example, a heart rate monitor can be associated with the body of the athlete 1 to detect the heartbeat of this latter and send information to the external control unit 4, which processes this information and modifies operation of the activation unit based on predetermined models.

According to an embodiment, each modular device 3 comprises a geolocation unit.

Once each modular device 3 is identified by a code and is provided with a geolocation unit, or any other unit adapted to detect positioning, it is possible to accelerate the procedure of arranging the modular devices 3 based on predetermined patterns stored in the external control unit 4.

According to a further embodiment, it is possible to provide a container for housing the modular devices 3, this container comprising circuits for recharging the batteries of the modular devices 3, said charge circuits being of wireless type.

This container, preferably made of methacrylate, will have electronics dedicated to simultaneous charging of all the batteries incorporated in the modular devices 3, for example through a contactless inductive device. Moreover, if the modular devices 3 are to be positioned permanently, it will be possible to wire the respective power supplies, again from this container.

Based on the logics described previously, a possible example of operation of the external control unit 4 will be dealt with below.

When started, the logical program from the external control unit 4 can have a first screen with the company logo and the possibility of accessing an editing submenu. Subsequently, a screen will appear in which it is possible to choose between 15 different preset programs.

A series of possible programs according to a preferred embodiment of the system of the present invention will be listed below. In the description below, the term "satellite" means a modular device 3 as described above.

Programs 01-04: Panel

The panel programs identify a type of training structured on 4 progressive levels of intensity. The switch on times of the modular devices 3, (latency times) vary from 1 second in the program "PANEL 1" to 0.3 seconds in the program "PANEL 4". If the satellites are not switched off in this interval of time, they will be switched off automatically and the counter will not increase. It will be possible to switch on two satellites simultaneously. Switching on of the satellites is programmed randomly. Switching off of the first satellite causes the switch on sequence to start.

The program can have a dual duration option:
time based (max 60 minutes);
shoot based (switch on/off) (max 1000).
The color of the lights is red.

Program 05: Multi-Stage Fitness or Beep Test

The Multi-stage fitness or Beep Test is performed by generating an alternation of switch ons between two satellites whose switch on frequency is gradually increased, obliging the athlete to increase his/her reaction speed. The two satellites are placed at a distance of 10 meters from each other. Initially the latency time is 4.5 seconds; after a certain number of switch ons (for example 20) this time will decrease obliging the athlete to accelerate his/her movements. A decrease of 0.2 seconds for each step is envisaged. If the athlete is unable to switch off a satellite three times in a row the test is concluded. The color of the two satellites will be green for 80% of the switch on time and will then change to red for the remaining 20%.

Program 06: Fix

In this program the satellites are positioned with a fixed starting and return point (pivot). The athlete must switch off a satellite and return to the starting point each time (go, switch off and come back logic). Switching on of the satellites subsequent to that of the base point is random. If a satellite is not switched off within the latency time of 30 seconds, the switch off is not counted. Switching on of a satellite is sequential to switching off of the previous satellite. Simultaneous switching on of two satellites is also possible.

The program can have a dual option:
time based (max 60 minutes);
shoot based (switch on/off) (max 1000).
It is possible to select six different colors of lights.

Program 07: Mobile

In this program the satellites are positioned in a free pattern and switching on is random. If a satellite is not switched off within the latency time of 30 seconds, the switch off is not counted. Simultaneous switching on of two satellites is also possible.

The program can have a dual option:
time based (max 60 minutes);
shoot based (switch off/on) (max 1000).
It is possible to select six different colors of lights.

Program 08: Combat

In this program satellites worn by a person (competitor) on one or more parts of the body are switched off.

The program can have a dual option:
time based (max 60 minutes);
shoot based (switch off/on) (max 1000).

The satellites are of two different colors (red and green) and will switch on simultaneously until, following contact by the competitor, one of the two will be switched off. A sound will signal allocation of the point and after two seconds the satellite that was switched off will be switched on again.

Program 09: Circuit

In this program the satellites are switched on sequentially in increasing order (for example from 1 to 12 with 12 satellites). The latency time is 30 seconds, after which the switch off will not be counted.

The program can have a dual option:
time based (max 60 minutes);
shoot based (switch off/on) (max 1000).

Program 10: Live

In this program each satellite, with any color, is switched on in real time and without a predetermined pattern. Two satellites can also be switched on simultaneously.

The program can have a dual option:
time based (max 60 minutes);
shoot based (switch off/on) (max 1000).

Also in this case the latency time is 30 seconds.

Program 11: Personal

A personal key will enable the choice of 15 personalized programs that can be edited in the editing session. Switch on patterns can be set choosing the color, the number of satellites to be switched on simultaneously (maximum two) and the latency time. Also in this case both the time option (max 60 minutes) and the shoot option (switch off/on, max 1000) are possible.

Program 12-15: Group

In this program, switch on of the satellites is divided into color groups, where the groups can be from two to six. The total number of satellites is divided equally into the various color groups. The choice of the number of color groups is implemented using specific keys. For example, if the group 2 key is selected, the satellites will be divided into two groups: from number 1 to 6 red, from number 7 to 12 green. Once all the satellites of one color have been switched off randomly, all those of the other color or of the subsequent color will be switched on again. Also in this case there are two duration options:
time based (max 60 minutes)
shoot based (switch on/off) (max 1000)

The latency time is always set at 30 seconds.

The performances of the athlete 1 are recorded by the external control unit 4 and are communicated to the trainer 2.

It is clear how the object of the system of the present invention is obviously that of encouraging the athlete 1 to switch off the greatest number of modular devices 3 in the shortest possible time.

In a screen of the results the graphs relating to each color in play must be displayed, showing the partial reactivities intended as number of modular devices 3 switched off with respect to the time taken to switch them off. The histogram graph must indicate the training time in percentage (%) on the abscissa and the reactivity values calculated in the various time percentage intervals in steps of 5 (5%, 10%, 15%, etc.) on the ordinate. The value of the total average reactivity, maximum and minimum, must be indicated in the graph. The same screen will also show the duration of the exercise and the shoot totalizer. A save key will allow the results to be stored in the database of the system. Naturally, if several colors were enabled for the exercise performed, the graphs will be visible in sequence by scrolling down the display 41.

The logical program also allows the training programs to be modified and set, via the editing session.

This session is accessed from the home screen and, after keying in a password, the following menus can be accessed:

Edit Program

This allows 15 completely personalizable user programs to be modified. It will be possible to establish the sequence of the satellites to be switched on, the related colors and the latency time for each satellite. The routines thus generated, once retrieved in the "person" user menu, will be executed cyclically for the whole of the set duration of the training session. Two satellites can be switched on simultaneously.

Check Satellites

In this procedure the satellites connected are checked in order to verify the presence and correct operation of the wireless connection between the various components of the system. The system will therefore interrogate each satellite, verifying the response in terms of communication. If a satellite does not respond correctly, even when the battery is flat, the system will automatically exclude this satellite from the various programs to prevent interruptions thereof.

Enable Beep

It is possible to choose three configurations of the buzzer: buzzer always off, buzzer active for 1 second when the satellite is switched on, buzzer active for 1 second when the satellite is switched off.

Enable Saving

Enables management of the archives to be able to save and retrieve previously executed training sessions for each single athlete/session.

Change Password

This allows the password of the setting menu to be changed. The system will prompt the user to enter the old password, followed by the new password, twice.

The invention claimed is:

1. A system for performing motor activity, comprising:
a plurality of modular devices (3);
one or more body sensors adapted to detect information from a body (2) of at least a trainer in charge of controlling the system, said one or more body sensors comprising a microphone associated with a voice-recognition system and a movement sensor configured to detect movements of said body that define gestures of the body of the trainer; and
an external control unit (4),
where each modular device (3) comprises at least:
means of generating at least one sensory stimulus (31) comprising at least one source for generation of light energy (31a);
an activation unit of said means of generating at least one sensory stimulus;
means of detecting a human reaction to said sensory stimuli (31); and
one or more position sensors mounted on the modular device (3) or on a supporting structure for said modular devices (3),
wherein said external control unit (4) comprises means for measuring the parameters acquired by said one or more body sensors and said one or more position sensors, and
wherein said external control unit (4) is configured to generate commands for the activation unit of at least a selected one of the modular devices (3) as a function of the parameters acquired by the aforesaid body sensors, so that the gestures of the body of the trainer and said voice commands of the trainer are detected by the external control unit (4) and, based on the detected gestures and based on the detected voice commands of the trainer, the external control unit (4) generates signals for activation of the at least selected one of the modular devices.

2. The system according to claim 1, wherein said position sensor comprises a geolocation sensor.

3. The system according to claim 1, wherein said body sensor comprises a biometric sensor for detecting a biometric parameter of the trainer.

4. The system according to claim 3, wherein said biometric sensor is a heart rate monitor.

5. The system according to claim 1, comprising at least one display unit (41) and an input-output interface.

6. The system according to claim 1, wherein said source for the generation of light energy (31a) comprises one or more LEDs.

7. The system according to claim 1, wherein said source for the generation of light energy (31a) comprises at least one display configured to project colors, images or messages.

8. The system according to claim 1, wherein said means of detecting a human reaction comprises at least one proximity sensor.

9. The system according to claim 1, wherein each of the plurality of modular device (3) has a rechargeable battery, the system comprising a container for housing the modular devices (3), said container comprising circuits for recharging the batteries of said modular devices (3).

10. The system according to claim 1, comprising a supporting structure that includes one or more movable supports on which one or more modular devices (3) of the system are mounted, said structure being equipped with one or more position sensors adapted to detect the position or the movements of one or more modular devices (3).

* * * * *